(12) United States Patent
Honda et al.

(10) Patent No.: US 6,598,006 B1
(45) Date of Patent: Jul. 22, 2003

(54) DATA INPUT DEVICE USING A PALATAL PLATE

(75) Inventors: Kiyoshi Honda, Kyoto (JP); Yutaka Ichinose, Kyoto (JP); Masahiko Wakumoto, Kyoto (JP)

(73) Assignees: Advanced Telecommunications Research Institute International, Kyoto (JP); Nitta Corporation, Osaka (JP)

( * ) Notice: Subject to any disclaimer, the term of this patent is extended or adjusted under 35 U.S.C. 154(b) by 120 days.

(21) Appl. No.: 09/690,383

(22) Filed: Oct. 17, 2000

(30) Foreign Application Priority Data

Oct. 18, 1999 (JP) ............................................. 11-295150

(51) Int. Cl.[7] .......................... H09B 1/034; A61B 5/10; A61C 3/00
(52) U.S. Cl. ...................... 702/116; 340/825.19; 433/6; 600/383; 600/534; 600/546
(58) Field of Search ........................ 702/42, 108, 116; 73/649; 340/825.19, 407, 539; 600/383, 534, 546; 433/6

(56) References Cited

U.S. PATENT DOCUMENTS

| | | | | |
|---|---|---|---|---|
| 4,334,542 A | * | 6/1982 | Takinishi et al. | ............ 600/383 |
| 4,629,424 A | * | 12/1986 | Lauks et al. | .................... 433/6 |
| 5,212,476 A | * | 5/1993 | Maloney | ................ 340/825.19 |
| 5,600,311 A | * | 2/1997 | Rice et al. | ............. 340/825.19 |
| 5,792,067 A | * | 8/1998 | Karell | ......................... 600/534 |
| 6,280,394 B1 | * | 8/2001 | Maloney et al. | ............ 600/546 |

* cited by examiner

*Primary Examiner*—John Barlow
*Assistant Examiner*—John Le
(74) *Attorney, Agent, or Firm*—Gerald T. Bodner

(57) ABSTRACT

A data input device uses a palatal plate formed of resin that includes multiple sensors. The sensors detect whether the palatal plate is in contact with the tongue or not. An output (on-off) of the sensor is supplied to an IC. The data corresponding to the output of the sensor, i.e. a form of the tongue-palate contact, are transmitted from the IC through an antenna to an external equipment.

18 Claims, 2 Drawing Sheets

DATA INPUT DEVICE USING A PALATAL PLATE

BACKGROUND OF THE INVENTION

1. Field of the invention

This invention relates to a data input device using a plate of resin covering the hard plate (palatal plate hereafter). More particularly, the invention is concerned with a data input device used to control an external equipment through a use of the tongue instead of the limb of the human body.

2. Description of the prior art

As a conventional device using a palatal plate of this kind, electric palatography devices are in practical use to detect the position where the tongue makes contact with the palate via electrodes arranged on the surface of the palate. This has made it possible to observe the manner the tongue contacts the palate. The palatography devices have been applied in the study of phonetic science and rehabilitation of the articulatory disorders.

However, this prior art is nothing more than observing a manner the tongue contacts the palate. Accordingly, no idea has existed to utilize the same device for controlling an external equipment.

SUMMARY OF THE INVENTION

Therefore, it is a primary object of the present invention to provide a novel data input device.

A data input device according to the present invention comprises: a palatal plate; a sensor provided on said palatal plate and for detecting at least whether the palatal plate is contacted by a tongue or not; a data transmitting apparatus for transmitting a sensor signal wirelessly to an outside.

In the data input device using the palatal plate, the sensor is provided on the palatal plate. The sensor detects whether contacted by the tongue or not. The data transmitting/receiving apparatus wirelessly transmits to the external equipment a sensor output, i.e. a sensor signal (data) according to a form the tongue is in contact with the sensor. The external equipment is controlled in processing or operation according to the sensor signal sent.

For example, if multiple on-off sensors are used, sensor signals of contact states represented by on and off are to be transmitted to the external equipment.

Also, if a pressure sensor is used, in addition to on-off detection, it is possible to detect the pressure applied by the tongue on the sensors (tongue–1=palate contact pressure). The external equipment can be controlled continuous (analogue) in processing or operation according to the sensor signal.

Furthermore, although the data transmitting/receiving apparatus may be provided in a position other than on the palatal plate, the provision within the palatal plate reduces the size of the apparatus main body.

According to the invention, because a sensor signal corresponding to the tongue contact state is, transmitted to an external equipment, the external equipment can be processed or operated in accordance with the present invention. That is, the external equipment can be controlled according to the tongue contact state.

The above described objects and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Figure 1:
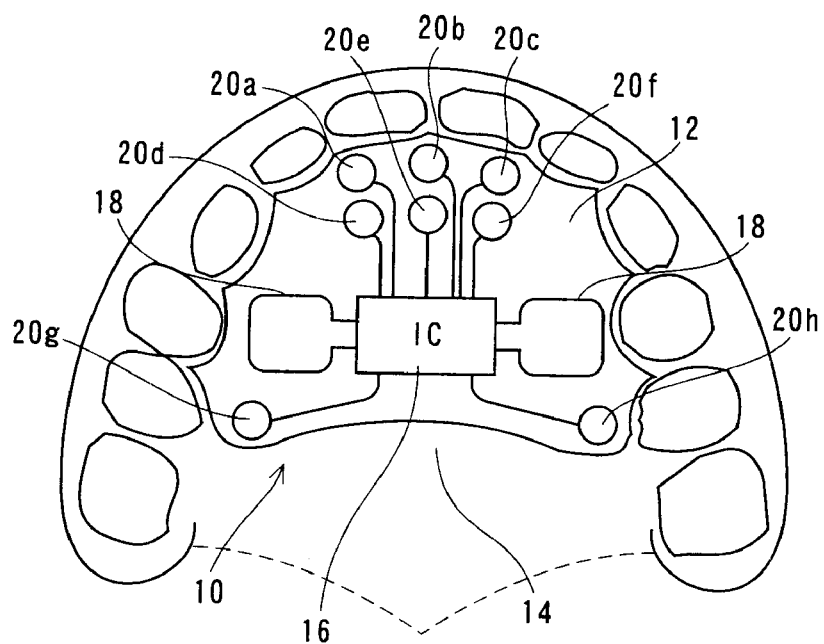
FIG. 1 is an illustrative view showing one embodiment of the present invention.

Referring to FIG. 1, a data input device using a palatal plate of this embodiment (hereinafter merely referred to as "data input device") 10 includes a palatal plate 12 formed of resin. The palatal plate 12, although illustrated in a planer form in FIG. 1, is formed actually in a nearly conical shape so that it is to be placed in close contact with a palate 14 of a wearer. On the palatal plate 12 are provided an IC 16, an antenna 18 and multiple (8 in this embodiment) of sensors 20a–20h. The antenna 18 and the sensors 20a –20h are connected to the IC 16. The sensors 20a–20h are arranged, for example, as shown in FIG. 1 but not limited in arrangement and the number to the embodiment. Also, the IC 16 and the antenna 18 are enclosed in a resin forming the palatal plate 12, as shown in FIG. 2.

Figure 2:
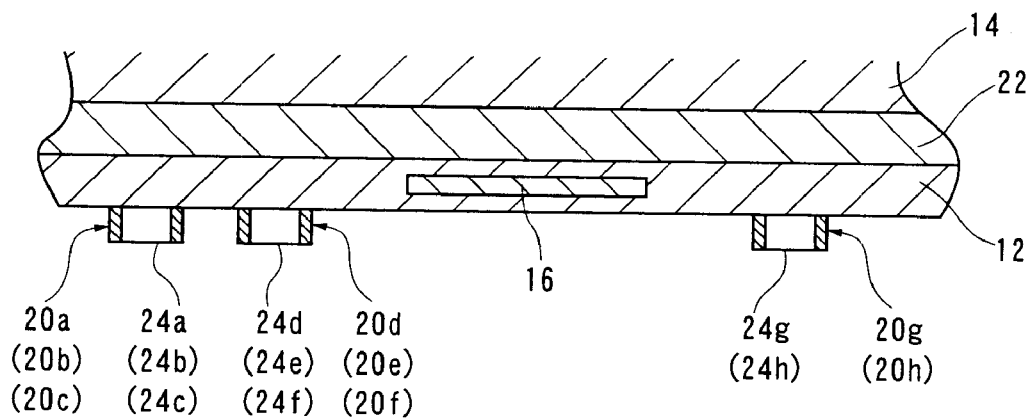
FIG. 2 is an illustrative view showing a palatal plate of the FIG. 1 embodiment.

Referring to FIG. 2, the palatal plate 12 is also provided with a palatal-side electrode 22 formed in a thin film form extending over the surface of the palate 14. Incidentally, the palatal-side electrode 22 is not necessarily formed on the entire surface of the palate 14 but may be provided in part thereof. The palatal-side electrode 22 is insulated from oral-side electrodes 24a–24h of the sensors 20a–20h through the palatal plate 12. The oral-side electrodes 24a–24h are also insulated from one another. Thus, the sensors 20a–20h shown in FIG. 1 are structured by the palatal-side electrode 22 and the oral-side electrodes 24a–24h. Consequently, these electrodes 22 and 24a–24h, although not shown in FIG. 2, are connected to the IC 16 enclosed in the palatal plate 12.

Incidentally, the oral-side electrodes 24a–24h are also formed in a thin film similarly to the palatal-side electrode 22. In FIG. 2, however, the palatal plate 12, the palate 14 and the palatal-side electrode 12 are depicted as planer surfaces for ease of understanding, i.e. they are depicted with thickness although they are actually in thin film forms. Furthermore, omittedly shown are connection lines connecting the IC 16 to the palatal-side electrode 22, the oral-side electrodes 24a–24h and the antenna 18.

When the tongue (not shown) contacts one of the oral-side electrodes 24a–24h shown in FIG. 2, an electric circuit is formed between the same one of the oral-side electrodes 24a–24h and the palatal-side electrode 22. This is because the palate 14 and the tongue are a part of the same human body. Consequently, the detection of an electric resistance of the circuit enables determination as to which one of the oral-side electrodes 24a–124h. In the example shown in FIG. 3, an electric resistance is detected as a voltage between an oral-side electrode 24a–24h and the palatal-side electrode 24. This provides recognition of an oral-side electrode 24a–24h which the tongue is currently in contact with.

In order to enable this, the oral-side electrodes 24a–24h are connected through respective signal lines to a multiplexer (MPX) 32 included in a data collection circuit 30. Due to this, the MPX 32 receives a voltage between each of the oral-side electrodes 24a–24h and the palatal-side electrode 22. This MPX 32 is switched under control of the CPU 38 to sequentially output input data as instructed by the CPU 38 (i.e. voltages from the oral-side electrodes 24a–24h).

The voltages between the oral-side electrodes 24a–24h and the palatal-side electrode 22 are sequentially outputted from the MPX 32, and inputted to an A/D converter 36 through a sample-and-hold (S/H) circuit 34. The A/D converter 36 is a 1-bit A/D converter to determine whether the voltage level sampled from each of the oral-side electrodes 24a–24h exceeds a threshold or not. When the voltage is equal to or greater than a predetermined threshold, "1" is outputted, while when smaller than the threshold "0" is outputted. In this manner, the data collection circuit 30 outputs data "1" or "0" representative of on/off for each oral-side electrodes 24a–24h.

The on/off signal concerning the oral-side electrode 24a–24h is supplied to a CPU 38. The CPU 38 includes a CPU core 38a and a memory 38b. The CPU core 38a temporarily stores the on/off data "1" or "0", on each oral-side electrode 24a–24h or sensor 20a–20h, to an input register (not shown) formed in a predetermined region of the memory 38b. That is, the CPU core 38a selects a voltage signal from the MPX 32 and at that time the A/D converter 36 outputs "1" or "0", depending upon which "1" or "0" on a designated oral-side electrode 24a–24h can be set onto the input register.

In this manner, the CPU 38 can detect a oral-side electrode 24a–24h that the tongue is in contact, i.e. a sensor 20a–20h (FIG. 1) now being in an on-state. Accordingly, when for example the sensors 20a, 20b and 20c only are in an on-state and the other sensors 20a–20h are in an off-state, data of "11100000" is inputted to a transmitting/receiving circuit 40.

The transmitting/receiving circuit 40 has a not-shown carrier generator circuit. The carrier (carrier wave) generated by the carrier generator circuit is modulated by the data mentioned above. The modulation signal (data) is radiated toward the external equipment 50, or external equipment antenna 54, through the antenna 18. On the other hand, the external equipment 50 transmits information data about the external equipment 50, i.e. data representative of an electric wheelchair when the equipment under control (external equipment 50) is for example an electric wheelchair. This information data is received by the antenna 18 and supplied to the CPU 38 through the transmitting/receiving circuit 40. Consequently, the CPU core 38a determines a to-be-used memory area (working area) on the memory 38b based on the information data about the external equipment 50 (data representing the equipment under control is an electric wheelchair in this example). That is, the working area on the memory 38b can be determined in accordance with a kind of the equipment under control.

Figure 3:
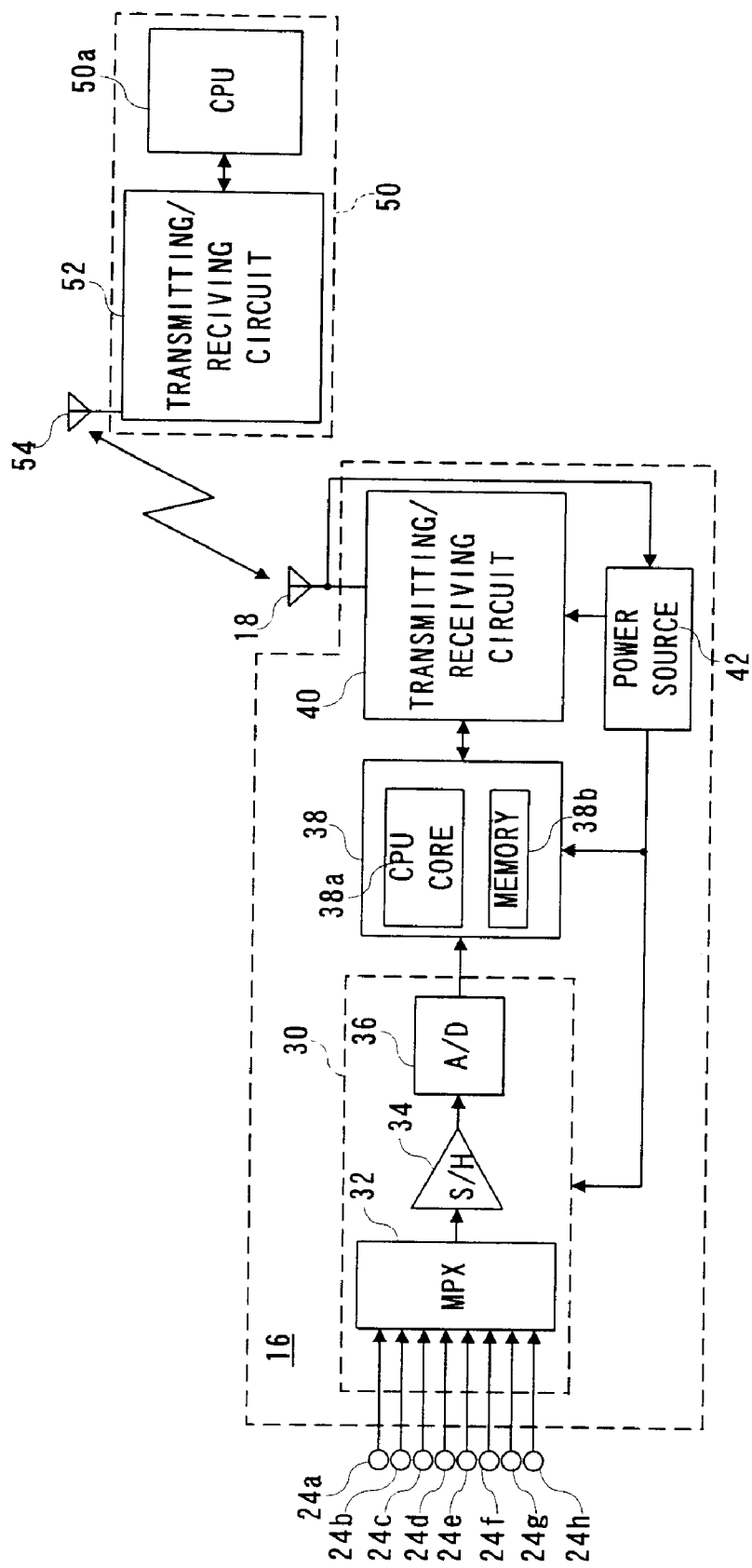
FIG. 3 is an illustrative view showing an IC used in the FIG. 1 embodiment.

Incidentally, the IC 16 shown in FIG. 3 incorporates therein a power source circuit 42. The power source circuit 42 has a rectifier circuit (not shown) to rectify a carrier (carrier wave) transmitted from a transmitting/receiving circuit 52 of the external equipment 50 through the antennas 54 and 18. The carrier transmitted from the external equipment 50 is rectified into direct-current voltage for charging a not-shown battery. From the battery, electric power is supplied to the above circuits 30, 38 and 40. However, The structure of the power source circuit 42 as above is mere one example. The power source circuit 42 may use only a battery (primary, secondary).

On the other hand, the external equipment 50 is controlled responsive to the data transmitted from the data input device 10, or IC 16, and includes a CPU 50a for enabling such control. The external equipment 50 includes a circuit (not shown) to be controlled by the CPU 50a and a transmitting/receiving circuit 52. The transmitting/receiving circuit 52 includes a demodulation circuit to demodulate a modulation signal transmitted from the IC 16 and reproduce data, and a modulation circuit to transmit data to the IC 16. The transmitting/receiving circuit 52 is connected to an antenna 54. The CPU 50a of the external equipment 50 controls the to-be-controlled circuit depending on an on/off-state of each sensor 'sent from the IC 16, according to a control program previously setup on the memory (not shown) of the CPU 50a.

Such control in usual cases is due to digital control discretely defined depending upon which one of the sensors is in an on-state. However, where two or more sensors 20a–20h are turned on, it is possible to provide analog control to be made depending upon a combination of the sensors or a magnitude of tongue contact area.

Incidentally, the transmitting/receiving circuit 52 of the external equipment 50 is used in access of the external equipment 50, or CPU 50a, to the IC 16, or CPU core 38a of the CPU 38, or to the memory 38b, in addition to sending a carrier for giving electric power to the IC 16 as stated before. In this case, by modulating the carrier by access data, the access data is to be demodulated by the transmitting/receiving circuit 40 of the IC 16 and supplied to the CPU 38.

In data transmission from the IC 16 and from the external equipment 50, the same frequency of a carrier may be used with different modulation schemes. Otherwise, different carrier frequencies may be used with the same modulation scheme. Otherwise, the both may be provided same by dividing the transmission time.

In this manner, the sensors 20a–20h use a type of sensors that is capable of detecting on-off state. However, if pressure sensors are used, it is possible to detect a contact pressure of the tongue in addition to detection as to which sensor 20a–20h is in contact with. In this case, the pressure sensors can utilize, for example, those of a strain-gauge scheme. Also, it is possible to utilize a sensor as described in PCT/JP98/03669 applied for an international patent by the present applicant, etc. Depending upon the change of contact pressure, electric resistance is varied between any discrete electrode 24a–24h in contact and the palatal-side electrode 22. A voltage proportional to the electric resistance is inputted to the MPX 32. Consequently, a voltage commensurate with the electric resistance is supplied to the A/D converter 36 through the S/H circuit 34. From the A/D converter 36, pressure data, e.g., of 3 bits, is inputted to the CPU 38. That is, a voltage value corresponding to a contact pressure is converted into pressure data, e.g. of "000" to "111", to be stored in the input register mentioned before. Incidentally, in this case, used is an A/D converter 36 having bits, e.g. 4 bits or 8 bits. It is needless to say however that, although pressure data in bit is arbitrary, the increase of bit number improves the resolving power.

Such pressure data on each oral-side electrode 24a–24h is transmitted to the external equipment 50. Accordingly, the CPU 50a can control the to-be-controlled circuit of the external equipment 50 according to a sensor with which the tongue is in contact as well as the magnitude or change of contact pressure.

For example, the data input device 10 is applicable as a data input device used for an electric larynx, an electric wheelchair, a computer, etc. In the case of using the data input device 10 in controlling an electric larynx, transmitted is data corresponding to on-off operation of the sensors 20a–20h during speech production, according to which vibration of the electric larynx is controlled. That is, voiceless consonant (sound without vocal fold such as p, k and t) is possible to produce. Also, where pressure sensors are used, contact pressure is also to be detected enabling voiced-voiceless distinction in a natural manner.

Also, where the data input device 10 is used in controlling an electric wheelchair, the sensors 20a–20h are assigned with respective directions. This enables operation by use of the tongue. For example, the sensor 20a is assigned as right forward, the sensor 20b as straight ahead and the sensor 20c as left forward. Also, the sensor 20d is as right backward, the sensor 20e as regression and the sensor 20f as left backward. Furthermore, the sensor 20g is for turning right and the sensor 20f as turning left. Accordingly, the electric wheelchair can be operated according to any of the sensors 20a - 20f the tongue contacts. In this case, forward and backward speeds are given by respective constant values. Direction only can be controlled by switching on-off the sensors 20a–20h. Meanwhile, when none of the sensors 20a–20h are not contacted by the tongue, the electric wheelchair halts. Consequently, if the tongue becomes out of contact with the sensor 20a–20h during movement of the electric wheelchair, brake operation is entered.

Also, when pressure sensors are used, contact pressure is also to be detected. This makes it possible to vary in continuous (analog) fashion the speed of the electric wheelchair and angle of turning left/right depending upon contact pressure (pressure data). That is, operation is possible in a manner using a steering wheel or accelerator of an automobile. Furthermore, deceleration, such as rapid brake, is also possible using changes in contact pressure.

Furthermore, where the data input device 10 is used in a computer, or wearable computer, or the like, the data input device 10 can be used just like a computer mouse. That is, the sensors 20a - 20f are assigned with respective directions, similarly to the case with the electric wheelchair. Specifically, the sensor 20a is assigned as upper right, the sensor 20b is as upper, and the sensor 20c is as upper left. Also, the sensor 20d is as lower right, the sensor 20e is as lower and the sensor 20f is as lower left. Furthermore, the sensor 20g is as rightward and the sensor 20h is as leftward. Consequently, when the tongue contacts a sensor 20a–20h, a mouse pointer on a monitor connected to the computer is moved in a responsive manner. This makes it possible to move the mouse pointer to a desired numeral or character being displayed on the monitor. Also, if two sensors are provided in addition to the sensors 20a–20h and further "OK" and "clear" are assigned correspondingly to the sensors, it is then possible to decide or correct an input numeral or character. Incidentally, the mouse pointer may be moved in a way of operation similar to that with a touch pad, if the number of sensors is increased furthermore.

According to this embodiment, because data is transmitted to an external equipment correspondingly to a tongue contact form, the external equipment can make processing or operation in accordance therewith. That is, the external equipment can be controlled responsive to tongue contact states.

Incidentally, the IC 16 shown in the embodiment can use multi I/O-type CMOS gate array, IC "BU123606L" produced by Rohm. Also usable are high-speed-type CMOS gate array, IC 2BU25306" by same and further CMOS cell-base IC family, IC "BU35S", "BU253S", "BU163S", etc. by same.

In the above embodiment, the palatal-side electrode 22 was formed on the palatal side (on the backside) of the palatal plate 12. However, the palate-side electrode 22 may be provided in an arbitrary position in the palate or further in a position of other than the palate, e.g. on the gum.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A data input device, comprising:
   a palatal plate;
   a tongue contact sensor provided on said palatal plate and for detecting at least whether said sensor is contacted by a tongue or not, wherein said tongue contact sensor includes a plurality of on-off tongue contact sensors; and
   a data transmitting apparatus for transmitting a sensor signal wirelessly to an outside location.

2. A data input device according to claim 1, wherein said data transmitting apparatus-is assembled on said palatal plate.

3. A data input device according to claim 1, wherein said data transmitting apparatus is assembled on said palatal plate.

4. A data input device, comprising:
   a palatal plate;
   a tongue contact sensor provided on said palatal plate and for detecting at least whether said sensor is contacted by a tongue or not, wherein said tongue contact sensor includes a pressure sensor; and
   a data transmitting apparatus for transmitting a sensor signal wirelessly to an outside location.

5. A data input device according to claim 4, wherein said data transmitting apparatus is assembled on said palatal plate.

6. A data-input device according to claim 4, wherein said data transmitting apparatus is assembled on said palatal plate.

7. A data transmitting/receiving system, comprising:
   a palatal plate;
   tongue contact sensor means provided on said palatal plate and for detecting at least whether the sensor means is contacted by a tongue or not;
   a first data transmitting apparatus situated proximately to said palatal plate for transmitting a sensor signal from said tongue contact sensor means wirelessly to an outside location remote from said palatal plate;
   a first data receiving apparatus situated remotely from said palatal plate for receiving a wireless signal transmitted from said first data transmitting apparatus;
   a second receiving apparatus situated proximately to said palatal plate for receiving at least one of wireless data and power signals; and
   a second transmitting apparatus situated remotely from said palatal plate for wirelessly transmitting said at least one of wireless data and power signals to the second receiving apparatus.

8. A system according to claim 7, wherein said tongue contact sensor means includes a plurality of tongue contact sensors, further comprising
   a data collection circuit for collecting the sensor signals from said plurality of tongue contact sensors, wherein said data transmitting apparatus wirelessly transmits the sensor signals collected by said data collection circuit.

9. A system according to claim 8, wherein said data collection circuit includes a multiplexer to receive the sensor signals from said tongue contact sensors and output a series of sensor signals and an A/D converter to convert said series of sensor signals into digital data, said first data transmitting apparatus wirelessly transmitting an output of said A/D converter.

10. A system according to claim 9, further comprising a control device to control an equipment under control according to data received by said first data receiving apparatus.

11. A system according to claim 10, wherein said equipment under control includes an electric wheelchair.

12. A system according to claim 9, wherein said first data receiving apparatus constitutes a computer mouse or similar one thereto.

13. A system according to claim 8, further comprising a control device to control an equipment under control according to data received by said first data receiving apparatus.

14. A system according to claim 13, wherein said equipment under control includes an electric wheelchair.

15. A system according to claim 8, wherein said first data receiving apparatus constitutes a computer mouse or similar one thereto.

16. A system according to claim 7, further comprising a control device to control an equipment under control according to data received by said first data receiving apparatus.

17. A system according to claim 16, wherein said equipment under control includes an electric wheelchair.

18. A system according to claim 8, wherein said first data receiving apparatus constitutes a computer mouse or similar one thereto.

* * * * *